United States Patent [19]
Dreyer

[11] Patent Number: 5,942,755
[45] Date of Patent: Aug. 24, 1999

[54] INFRARED OPTICAL GAS-MEASURING SYSTEM

[75] Inventor: Peter Dreyer, Pansdorf, Germany

[73] Assignee: Drägerwerk AG, Lübeck, Germany

[21] Appl. No.: 08/920,127

[22] Filed: Sep. 2, 1997

[30]    Foreign Application Priority Data

Feb. 19, 1997 [DE] Germany ............... 197 06 464
Apr. 17, 1997 [DE] Germany ............... 197 16 061

[51] Int. Cl.⁶ .................. G01N 21/35; G01N 21/31; G01N 21/61
[52] U.S. Cl. ................ 250/339.13; 250/339.12; 250/343
[58] Field of Search ................. 250/339.13, 343, 250/339.12

[56]          References Cited

U.S. PATENT DOCUMENTS

| | | | |
|---|---|---|---|
| 4,772,790 | 9/1988 | Aldridge | 250/343 |
| 4,899,053 | 2/1990 | Lai et al. | 250/343 |
| 4,914,719 | 4/1990 | Conlon et al. | 250/339 |
| 5,130,544 | 7/1992 | Nilsson | 250/343 |

FOREIGN PATENT DOCUMENTS 41 33 481 C2    4/1993    Germany.
195 20 488 C1   9/1996    Germany.

OTHER PUBLICATIONS

H. Riris, C. B. Carlisle, D.F. McMillen, and DE. Cooper, Aug. 20, 1996, Explosives detection with a frequency modulation spectrometer, *Applied Optics*/Vo. 35, No. 24.

*Primary Examiner*—Constantine Hannaher
*Assistant Examiner*—Albert Gagliardi
*Attorney, Agent, or Firm*—McGlew and Tuttle, P.C.

[57]          ABSTRACT

An infrared optical gas-measuring system with two infrared radiation sources (1, 2) and with at least one multispectral sensor (5). The system is suitable for determining the concentrations of different components of a gas flow. The two infrared radiation sources (1, 2) radiate in different spectral ranges with two different cycle frequencies $f_1$, $f_2$. The rays emitted are first passed through a radiation coupler (3), after which they pass through the gas flow to be measured, which is limited by windows (8), at right angles to the direction of flow. The rays finally enter a multispectral sensor (5), of which there is at least one, for measuring the intensity.

14 Claims, 1 Drawing Sheet

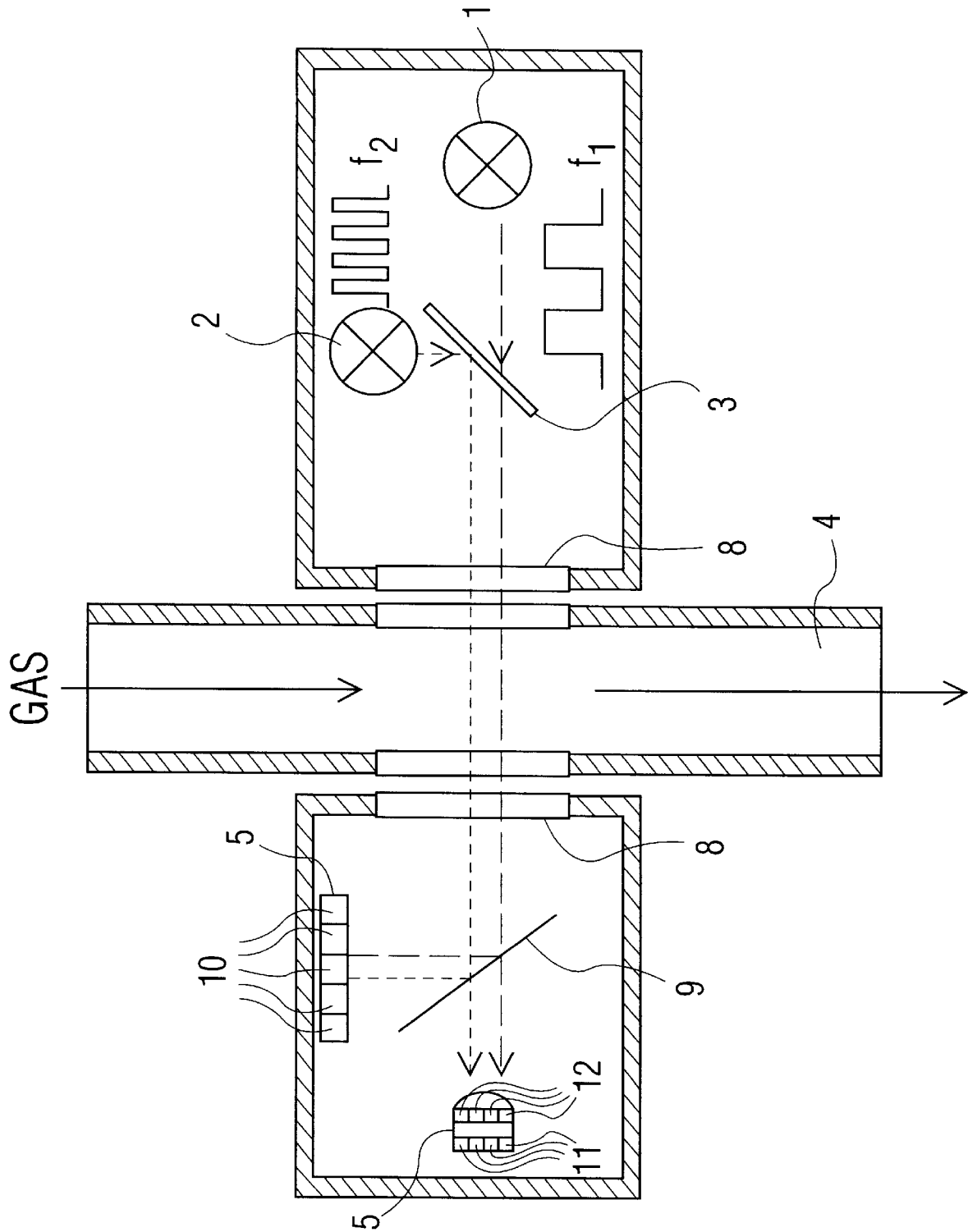

INFRARED OPTICAL GAS-MEASURING SYSTEM

FIELD OF THE INVENTION

The present invention pertains to an infrared optical gas-measuring system with two infrared radiation sources and with at least two infrared radiation detectors.

BACKGROUND OF THE INVENTION

Such measuring systems have been known from various publications and are suitable, depending on the wavelength range used, for measuring the concentrations of gases, e.g., for the measurement of $CO_2$ or also for determining the concentration of alcohol in the exhaled air of a human.

A measuring device of this class is described in DE 195 20 488 C1, in which the gas to be measured flows by diffusion into the hollow guide used as the measuring path.

A multispectral sensor for the infrared range has become known from DE 41 33 481 C2 corresponding to U.S. Pat. No. 5,300,778, in which different spectral ranges of a radiation to be measured are detected by separate detectors, wherein a compact design with high measuring sensitivity and accuracy is said to be possible.

SUMMARY AND OBJECTS OF THE INVENTION

The primary object of the present invention is to improve a gas-measuring system of the above-described type such that a gas flow consisting of a plurality of components can be measured rapidly in terms of the type and the concentration of these components.

According to the invention, an infrared optical gas-measuring system is provided with two infrared radiation sources and with at least two infrared radiation detectors. The two infrared radiation sources radiate in different spectral ranges with two different cycle frequencies $f_1$, $f_2$. The emitted rays are first passed through a radiation coupler and they subsequently pass through the gas flow to be measured. The gas flow, at right angles to the direction of flow, is limited by windows. The emitted rays then finally enter the multispectral sensor, of which there is at least one. The multispectral sensor has at least four infrared radiation detectors, for the measurement of the intensity of the emitted rays.

The first infrared radiation source preferably radiates in the spectral range of 7.5 to 14 $\mu$m and the second infrared radiation source preferably radiates in the spectral range of 2.5 to 4.3 $\mu$m. The cycle frequency $f_2$ of the second infrared radiation source is higher than the cycle frequency $f_1$ of the first infrared radiation source.

The first infrared radiation source may be used to measure the concentration of gaseous anesthetics in the respiratory flow. The second infrared radiation source may be used to measure the concentrations of $CO_2$ and $N_2O$ in the respiratory flow resolved for individual breaths.

The multispectral sensor has a radiation mixer and preferably exactly four infrared radiation detectors with corresponding different upstream infrared filters adapted to the absorption bands of the gases to be measured. Such a multispectral sensor is described in U.S. Pat. No. 5,300,778. The at least one multispectral sensor is preferably provided with at least one semiconductor detector. Two multispectral sensors may be used, wherein these are preferably arranged at right angles to one another, and the radiation from the two infrared radiation sources is split by a beam splitter between the two multispectral sensors corresponding to the wavelength ranges of the said two infrared radiation sources.

One essential advantage of the present invention is that an inexpensive, yet rapid gas-measuring system, with which the measurement of the concentrations of a plurality of components of a flowing gas volume is possible, is made available by means of a simple design. An especially preferred example of such an application is the measurement of gaseous anesthetics, $N_2O$ and $CO_2$, in the flowing exhaled or inhaled air of a patient. Such measurements are of great significance for the observation and the performance of anesthesia, especially in connection with operations. It is especially desirable in this connection to make possible the measurements of the relevant gases relative to a single breath. The essence of the present invention is the use of two-band infrared radiation sources, wherein one radiation source is used for measurement in the lock-in process in the spectral range of 7.5 to 14 $\mu$m and the second radiation source is used in the lock-in process in the spectral range of 2.5 to 4.3 $\mu$m with a higher cycle frequency for the measurement of $CO_2$ and $N_2O$ resolved for individual breaths. The radiations emitted are converged via a common radiation coupler, passed through a sample holder containing the gas mixture flowing through and subsequently measured with a plurality of infrared radiation detectors in at least one multichannel sensor, which comprises a radiation mixer and a plurality of, especially four infrared detectors, preferably pyroelectric detectors or quantum detectors, with various corresponding infrared filters adapted to the absorption bands of the gases to be measured.

One exemplary embodiment of the present invention will be explained on the basis of the drawing, which shows the basic structure of a gas-measuring system according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWINGS

In the drawings:

The only FIGURE is a schematic view of the infrared optical gas-measuring system according to the invention.

DESCRIPTION OF THE PREFERRED EMBODIMENTS

The FIGURE shows schematically an arrangement according to the present invention for the infrared absorption measurement of gases, which comprises a first, broad-band infrared radiation source 1 with a cycle frequency $f_1$ for a first spectral range $\Delta\Lambda_1$ as well as a second infrared radiation source 2 with the cycle frequency $f_2$ for a second spectral range $\Delta\Lambda_2$. The radiation of the two radiation sources 1, 2 are first passed through a radiation coupler 3, then through a sample holder 4, through which the gas mixture to be measured flows. The sample holder 4 has windows 8 transparent to infrared radiation. The radiation is finally measured with a multispectral sensor 5 in order to finally determine the concentrations of components of the gas mixture by a prior-art measurement of the radiation intensity.

The multispectral sensor 5 preferably comprises four individual radiation detectors 11, on or before which narrow-band infrared filters 12 are arranged. These filters let through one light wavelength for the selective measurement of a characteristic gas that is characteristic for this wavelength. Upstream scattering grids are used for reflection and radiation mixing.

The entire arrangement is accommodated in a hermetically sealed housing. This measuring unit may be used for the measurement of specific gases by means of the narrow-band infrared filters used. It is possible, e.g., to equip a measuring unit with specific infrared detectors and infrared filters for the measurement of $CO_2$, $N_2O$ and a reference wavelength. For another application, the arrangement may be provided with a detector unit for the measurement of gaseous anesthetics. It is possible in the preferred application to measure $CO_2$ and $N_2O$ possibly resolved for the individual breath for monitoring the patient. To meet this requirement, a sufficiently rapid measurement method with a time resolution of about 100 to 200 msec is required. The cycle frequency of the infrared radiation source of the lock-in measurement method used must consequently be at least 20 Hz. Since only thermal radiation sources with a relatively high, i.e., slow time constant are currently available at reasonable costs for such applications, the modulation amplitude is too small for a sufficient signal-to-noise ratio when they are used because of the above-mentioned cycle frequencies. So-called microincandescent lamps with thin tungsten filaments, i.e., small thermal masses, which are sealed airtightly in a quartz bulb, proved to be suitable. Even though the modulation amplitude is consequently reduced by the inertia of the filament, it can be built up sufficiently due to the high filament temperature (about 2,000° C.). The drawback of such components, which are available with quartz bulb only, is the limited spectral range. The radiation source is not suitable for use toward longer wavelengths any more because of the high attenuation of the infrared radiation by the quartz bulb beginning from 4.3 μm, but the measurement of $CO_2$ and $N_2O$ can be performed with a reference wavelength in a wavelength range of $\Delta\Lambda_2 < 4.3$ μm. Another practical application is the measurement of anesthetics. The measurement of these gases resolved for the individual breath is not absolutely of interest, but the analysis or the recognition of the anesthetics based on the characteristic infrared absorption bands is desirable. This circumstance requires a good signal-to-noise ratio (high modulation amplitude of the radiation source) and measurement in a spectral range in which the relevant gases have intense absorption with sufficient bands that are spaced apart in a gas-specific manner. The spectral range between 7.5 μm and 14 μm is especially suitable for this. A broad-band thermal infrared radiation source 1 emitting in this wavelength range with a cycle frequency $f_1$ is therefore arranged for the measurement of the anesthetics according to the FIGURE such that the emitted radiation falls through the sample holder 4 on the multispectral sensor 5 via a radiation coupler 4 transparent to $\Delta\Lambda_1$ and $\Delta\Lambda_2$. The detector in the multispectral sensor 5 is also used as a reference for the measurement of the gaseous anesthetic in the wavelength range of $\Delta\Lambda_2$, but this time with the radiation of the infrared radiation source 1 having the frequency $f_1$. Changes caused by contamination of the system or of the sample holder in the signal are compensated with a reference signal. The infrared radiation source 2 with the higher cycle frequency $f_2$ is arranged such that the radiation emitted by it falls on the detector unit in the multispectral sensor 5 through the sample holder 4 via the radiation coupler 3, which acts as a reflector for the wavelength range $\Delta\Lambda_2$.

By calculating the ratio of the two reference signals, it is also possible to measure and recognize changes in the two radiation sources, which usually depend on aging. The arrangement described would be able to be expanded with a beam splitter 9 and another detector unit in the form of a multispectral sensor 5, so that the number of gases that can be measured would increase as a result, or it would be possible to recognize the type of gas.

To increase the measurement performance, the detector unit may optionally be equipped with detector units that are equipped with semiconductor detectors 10 instead of pyroelectric measuring elements. These have higher sensitivity and lower time constants, but are more expensive.

While specific embodiments of the invention have been shown and described in detail to illustrate the application of the principles of the invention, it will be understood that the invention may be embodied otherwise without departing from such principles.

What is claimed is:

1. An infrared optical gas-measuring system, comprising:
   two infrared radiation sources radiating in different spectral ranges with two different cycle frequencies $f_1$, $f_2$;
   a radiation coupler, emitted rays from said radiation sources being first passed through said radiation coupler;
   sample holding means for holding a gas flow to be measured, said holding means being limited by windows, said emitted rays passing through said gas flow, at right angles to a direction of said gas flow, subsequent to passing through said radiation coupler;
   a multispectral sensor, including at least four infrared radiation detectors, for the measurement of the intensity of said emitted rays, after said emitted rays have passed through said gas flow.

2. The infrared optical gas-measuring system in accordance with claim 1, wherein a first of said infrared radiation sources radiates in the spectral range of 7.5 to 14 μm and a second of said infrared radiation sources radiates in the spectral range of 2.5 to 4.3 μm, and that a cycle frequency $f_2$ of said second infrared radiation source is higher than a cycle frequency $f_1$ of said first infrared radiation source.

3. The infrared optical gas-measuring system in accordance with claim 2, wherein said gas flow is a respiratory flow and said first infrared radiation source measures a concentration of gaseous anesthetics in the respiratory flow and said second infrared radiation source measures a concentrations of $CO_2$ and $N_2O$ in the respiratory flow, resolved for individual breaths.

4. The infrared optical gas-measuring system in accordance with claim 1 wherein said multispectral sensor has a radiation mixer and exactly four infrared radiation detectors with corresponding different upstream infrared filters adapted to the absorption bands of the gases to be measured.

5. The infrared optical gas-measuring system in accordance with claim 1 wherein said multispectral sensor is provided with at least one semiconductor detector.

6. The infrared optical gas-measuring system in accordance with claim 1 wherein another multispectral sensor is provided such that two multispectral sensors are used and the radiation from said two infrared radiation sources is split by a beam splitter between said two multispectral sensors corresponding to the wavelength ranges of said two infrared radiation sources.

7. The infrared optical gas-measuring system in accordance with claim 1 wherein said two multispectral sensors are arranged at right angles to one another.

8. An infrared optical gas-measuring system, comprising:
   a first infrared radiation source radiating in a first spectral range with a first cycle frequency $f_1$ and having a first time constant, said first spectral range including a characteristic wavelength of a first gas;

a second infrared radiation source radiating in a second spectral range with a second cycle frequency $f_2$ and having a second time constant, said second spectral range including a characteristic wavelength of a second gas, said first cycle frequency and said first time constant being different from said second cycle frequency and said second time constant;

a radiation coupler combining radiation from said first and second radiation sources into a combined radiation beam;

sample holding means for holding a gas flow to be measured in said combined radiation beam;

a multispectral sensor, including a plurality of infrared radiation detectors, for the measurement of the intensity of said characteristic wavelengths of said first and second gases after said combined radiation beam has passed through said gas flow.

9. A system in accordance with claim 8, wherein:

said multispectral sensor using a measurement method for said second gas requiring a second gas measurement cycle frequency;

said time constant of said first radiation source producing a modulation amplitude at said second gas measurement cycle frequency below a require signal-to-noise ratio;

said second radiation source being incapable of producing said characteristic wavelength of said first gas.

10. A system in accordance with claim 8, wherein:

said first spectral range includes characteristic wavelengths for a first set of gases and a reference wavelength;

said second spectral range includes characteristic wavelengths for a second set of gases;

said multispectral sensor and said infrared radiation detectors measure intensity of said characteristic wavelengths of said first and second set of gases and a reference wavelength after said combined radiation beam has passed through said gas flow.

11. A system in accordance with claim 10, wherein:

said first set of gases include gaseous anesthetics;

said second set of gases include $CO_2$ and $N_2O$.

12. A system in accordance with claim 8, wherein:

said second radiation source is a microincandescent lamp with a tungsten filament sealed in a quartz bulb, said microincandescent lamp operates with a filament temperature of approximately 2,000 degrees Celsius;

a modulation amplitude of said microincandescent lamp being limited by inertia of said filament.

13. A system in accordance with claim 9, wherein:

said second radiation source is a microincandescent lamp with a tungsten filament sealed in a quartz bulb, said microincandescent lamp operates with a filament temperature of approximately 2,000 degrees Celsius;

a modulation amplitude of said microincandescent lamp being limited by inertia of said filament.

14. A system in accordance with claim 13, wherein:

said first spectral range includes characteristic wavelengths for a first set of gases and a reference wavelength;

said second spectral range includes characteristic wavelengths for a second set of gases;

said multispectral sensor and said infrared radiation detectors measure intensity of said characteristic wavelengths of said first and second set of gases and a reference wavelength after said combined radiation beam has passed through said gas flow;

said first set of gases include gaseous anesthetics;

said second set of gases include $CO_2$ and $N_2O$.

* * * * *